United States Patent [19]

Pizon et al.

[11] Patent Number: 4,459,977
[45] Date of Patent: Jul. 17, 1984

[54] CORONARY SINUS RETROPERFUSION APPARATUS FOR THE TREATMENT OF MYOCARDIAL ISCHEMIA

[76] Inventors: Véronique Pizon, 7, rue Nicolas Houël, F-75005 Paris; Jean-Christian Farcot, 39, rue Spontini, F-75016 Paris, both of France

[21] Appl. No.: 350,381

[22] Filed: Feb. 19, 1982

[30] Foreign Application Priority Data

Mar. 27, 1981 [FR] France .............................. 81 06160

[51] Int. Cl.³ ............................................ F16K 15/00
[52] U.S. Cl. .................................... 128/1 D; 128/344; 604/102
[58] Field of Search ........................ 128/344, 346, 1 D; 604/97, 102; 3/1.7

[56] References Cited

U.S. PATENT DOCUMENTS

| 3,457,909 | 7/1969 | Laird ................................... 128/1 D |
| 3,656,873 | 4/1972 | Schiff ............................ 128/1 D X |
| 3,855,995 | 12/1974 | Bentley .............................. 128/1 D |
| 3,955,557 | 5/1976 | Takagi ................................. 3/1.7 X |
| 3,985,123 | 10/1976 | Horzlinger et al. ........... 128/1 D X |
| 4,250,872 | 2/1981 | Tamari .............................. 128/1 D |
| 4,277,706 | 7/1981 | Isaacson ........................ 128/1 D X |
| 4,337,775 | 7/1982 | Cook et al. ........................... 604/97 |

FOREIGN PATENT DOCUMENTS 2029236 3/1980 United Kingdom ............... 128/1 D
812295 3/1981 U.S.S.R. ............................. 128/1 D

OTHER PUBLICATIONS

Bregman et al., "Counterpulsation . . . in Open Heart Surgery", Med. Instrum., vol. 10, No. 5, Sep.-Oct., 1976, pp. 232-238.
Zwart et al., "First Clinicat . . . Bypass", vol. XVI, Trans. Amer. Soc. Art, F. Int. Organs, 1970, pp. 386-391.

Primary Examiner—Edward M. Coven
Attorney, Agent, or Firm—Young & Thompson

[57] ABSTRACT

An apparatus for diastolic blood retroperfusion of the coronary sinus in synchronism with the heartbeat rate for the treatment of infarctions. A connecting tube between an artery and the coronary sinus is fitted with a balloon-type catheter. A pulsatile unit mounted on the tube is controlled by an electrovalve in dependence on an electronic console and in synchronism with the patient's electrocardiogram (ECG) in order to retroperfuse arterial blood in the coronary sinus during diastoles and to permit the return flow of vitiated blood to the lungs during systoles. The apparatus permits diastolic retroperfusion of arterial blood in synchronism with the patient's electrocardiogram with maximum safety.

20 Claims, 21 Drawing Figures

FIG_1

FIG_2

FIG_3

FIG_4

FIG_5A

FIG_5B

FIG_6B

FIG_6A

FIG_7A

FIG_7B

FIG_8

Fig. 11

CORONARY SINUS RETROPERFUSION APPARATUS FOR THE TREATMENT OF MYOCARDIAL ISCHEMIA

This invention relates to an apparatus for blood retroperfusion which is primarily intended for the treatment of infarctions by injection of arterial blood into the coronary sinus in synchronism with the heartbeat rate.

It is known that the term retroperfusion designates the process which consists in sending oxygenated blood through the veins to an area in which it is needed. Since the veins extend from the heart, the blood flows within the veins from the heart to the periphery. Retroperfusion therefore consists in irrigating an area in the direction opposite to the normal blood flow.

In order to carry out retroperfusions and especially in order to combat the consequences of coronary insufficiencies, it is a known practice to use catheters.

The correct use of these catheters calls for the operation of complex equipment in order to carry out injections of blood in synchronism with the beat rate of the patient's heart.

The aim of the invention is to produce a blood retroperfusion apparatus which is capable of injecting blood in predetermined quantity and in perfect synchronism with the heartbeats and in particular although not exclusively into the coronary sinus by withdrawing blood at high pressure from a suitably selected artery of the patient. This quantity of blood must be injected during the diastole and reach a remote region of the coronary sinus in which a catheter is placed, the device being intended to permit a return to the general circulation of the vitiated blood after this latter has delivered oxygen to a region in which oxygen had previously been deficient.

The blood retroperfusion apparatus comprises in accordance with the invention:

a connecting tube between an artery and the zone to be irrigated, that is, the coronary sinus in the event that the apparatus is employed for the treatment of an infarction, that end of said tube which terminates in the coronary sinus being provided with a flexibleballoon catheter;

a pulsatile unit arranged on said tube and connected to control means whereby a predetermined quantity of oxygenated blood can be driven periodically by said unit towards the catheter;

an electronic device for maintaining the pulsatile unit and its control means in step with the patient's heartbeat, said device being synchronized with the electrocardiogram of the patient in order to control the injection of blood into the coronary sinus during diastole by means of the pulsatile unit and to allow the vitiated blood to flow back in the opposite direction during systole.

The principle of the equipment contemplated by the invention therefore consists in collecting arterial blood at high pressure via the aforementioned tube which terminates in the coronary sinus in the case of treatment of an infarction, and in injecting a predetermined quantity of blood at each diastole and in synchronism with the patient's heartbeat, this synchronization being ensured by the electronic device for controlling the pulsatile unit which operates as a pump, in dependence on the patient's electrocardiogram which is recorded at the same time as the retroperfusion.

The arterial blood at high pressure (100 mm of mercury) is therefore injected into the patient's venous system at low pressure (30 mm of mercury) at each diastole, the return of vitiated blood during each systole being of course permitted by the electronic device.

In one embodiment of the invention, the pulsatile unit comprises an inflatable flexible envelope forming an integral part of the tube and adapted to communicate at one end with the high-pressure arterial system and at the other end with the low-pressure venous system, and a rigid enclosure within which the flexible envelope is housed in leak-tight manner. Said enclosure is connected to said control means via a pipe which can be alternately filled with compressed gas and evacuated under the action of said control means, thus having the effect of exerting a correlative compressive force on the flexible envelope which is filled with arterial blood, of driving the blood towards the catheter and then of interrupting the flow of blood towards the catheter by initiating a further inflation of the envelope with arterial blood.

By modulating the pressure of compressed gas and the resultant vacuum in correlation with the patient's heartbeat, it is possible to optimize a number of factors:

the quantity of blood injected during diastole (which must be of minimum value in order to prevent subsequent difficulties);

the blood injection pressure regime;

the production of a unidirectional jet towards the arterial-blood infarction zone by means of the balloon catheter employed.

In another embodiment of the invention, the electronic device for follow-up control of retroperfusion comprises:

(a) an amplifier for continuously displaying the analog curve of the patient's electrocardiogram on the screen of a console;

(b) an analog-to-digital converter connected to the amplifier for displaying digital signals corresponding to the curve of the electrocardiogram on the screen of the console;

(c) a delay device connected to the converter and capable of delaying the digital signals corresponding to the systoles while the signals thus delayed are displayed on the screen and represented by a curve;

(d) a trigger circuit connected to the delay device and capable of generating a command signal for initiating the operation of an electrovalve which controls the pulsatile unit, said trigger circuit being turned-on by a signal from the delay device during a systole;

(e) elements for displaying on the screen the real curve of the consecutive pressure variation within the electrovalve and the real curve of the retroperfusion blood flow.

Starting from the patient's electrocardiogram, different signals are thus emitted and processed within the electronic device which computes the different parameters required for controlling the pulsatile unit in synchronism with the electrocardiogram in order to optimize the blood jets which are passed into the coronary sinus during diastoles.

The equipment according to the invention therefore comprises a particularly improved electronic system for carrying out synchronized diastolic retroperfusion of the coronary sinus, this being only one example of the different possible applications of said equipment.

Other features of the invention will be more apparent upon consideration of the following description and accompanying drawings in which a number of embodiments of the apparatus according to the invention are shown by way of example without any limitation being implied, and in which.

Figure 1:
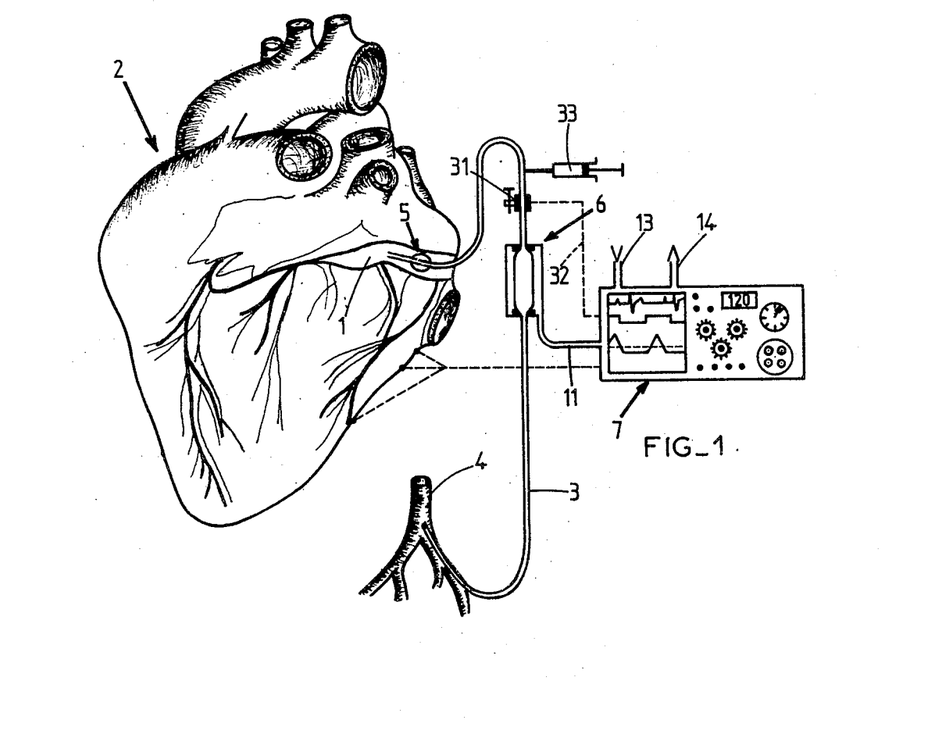
FIG. 1 is a general diagrammatic view illustrating the principle of the blood retroperfusion apparatus according to the invention, said apparatus being connected on the one hand to an artery and on the other hand to the coronary sinus of the heart to be irrigated.
Figure 2:
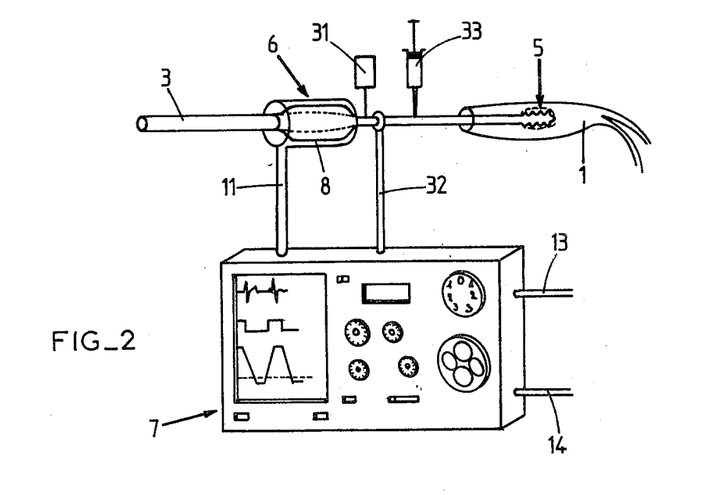
FIG. 2 is a view in perspective to a larger scale showing the apparatus according to the invention and in particular a control console which contains the electronic follow-up control device.

Referring to FIGS. 1 and 2, there is shown an apparatus for blood retroperfusion which is intended primarily but not exclusively for the treatment of myocardial infarctions by injection of arterial blood into the coronary sinus in synchronism with the patient's heartbeat rate.

Figure 6A:
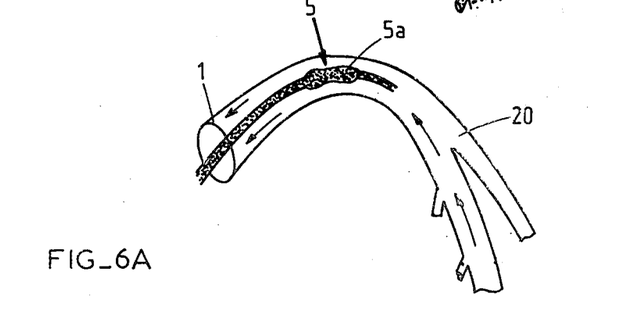
FIG. 6A is a detail view in perspective showing the balloon catheter within the coronary sinus during systole.
Figure 6B:
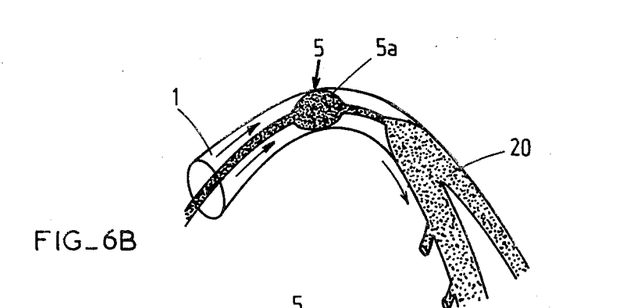
FIG. 6B is a view which is identical with the preceding but shows the catheter in the inflated state during diastole.
Figure 8:
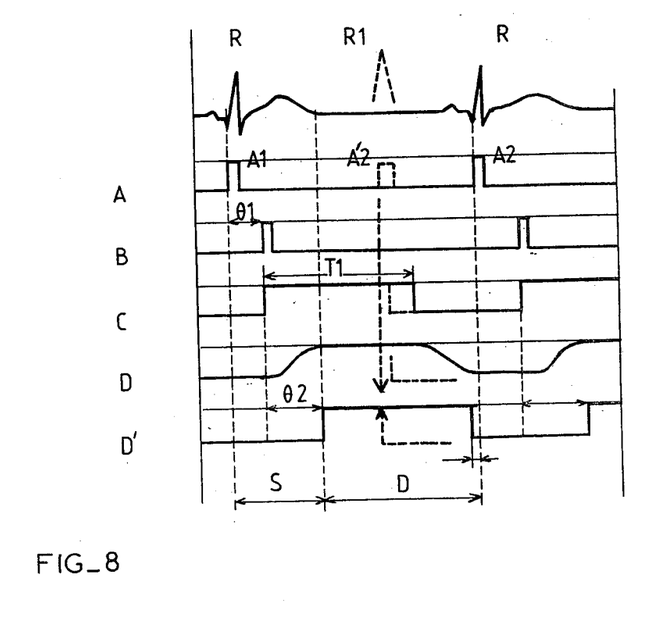
FIG. 8 shows all the curves displayed on the monitoring screen of the console which contains the electronic follow-up control device.

In the application which is illustrated in the drawings, said apparatus irrigates the coronary sinus 1 of the heart 2 of a patient who suffers from an infarction. According to the invention, the apparatus comprises the following essential elements:

(a) a flexible tube 3 providing a connection between an artery 4 (for example the femoral artery) and the zone to be irrigated, that is, the coronary sinus 1 in the application under consideration. That end of the tube 3 which is introduced in the coronary sinus 1 is fitted with a catheter 5 having a flexible balloon 5a (as shown in FIGS. 6A and 6B);

(b) a pulsatile unit 6 arranged on the tube 3 and connected to control means for periodically driving towards the catheter 5 a predetermined quantity of arterial blood supplied from the artery 4;

(c) an electronic follow-up control device which serves to operate the pulsatile unit 7 and its control means in dependence on the patient's heartbeat rate and which is housed within a console 7. Said electronic device is synchronized with the electrocardiogram (ECG) of the patient (as shown in FIGS. 2 and 8) in order to permit the pulsatile unit 6 to control the injection of blood into the coronary sinus 1 during one diastole of the cardiac cycle and to allow the vitiated blood to flow back in the opposite direction during a systole.

Figure 5A:
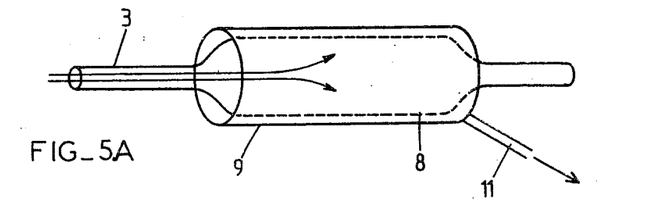
FIG. 5 is a double view in perspective showing the pulsatile unit, on the one hand during systole and on the other hand during diastole.
Figure 5B:
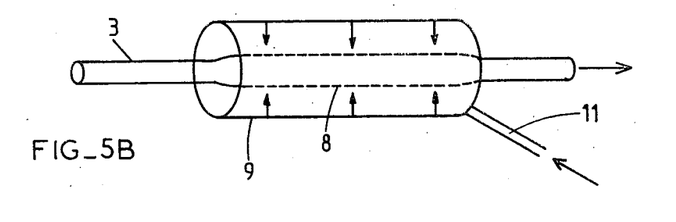

As shown in FIGS. 2 and 5, the pulsatile unit 6 comprises an inflatable flexible envelope 8 which forms an integral part of the tube 3. Said envelope communicates at one end with the arterial system 4 at high pressure (100 mm of mercury) and at the other end with the venous system at low pressure (30 mm of mercury). The flexible envelope 8 is preferably formed of suitable plastic material. The pulsatile unit 6 further comprises a rigid enclosure 9 formed of a cylinder in the example herein described, the envelope 8 being housed within said cylinder in leak-tight manner. The enclosure 9 is connected to the aforesaid control means via a pipe 11 which can be alternately filled with compressed gas such as air, for example, and evacuated under the action of said control means. In consequence, when compressed gas is passed into the pipe 11, said gas fills the intercalary space between the envelope 8 and the cylinder 9, compresses the envelope 8 and discharges the arterial blood contained within said envelope in the direction of the low-pressure venous system (coronary sinus 1). Conversely, when a vacuum is created within the pipe 11, the envelope 8 is inflated and filled with arterial blood.

Inflation of the envelope 8 is illustrated in the portion A of FIG. 5 whereas compression of said envelope accompanied by discharge of the blood contained within this latter is illustrated in the portion B of FIG. 5.

Figure 3:
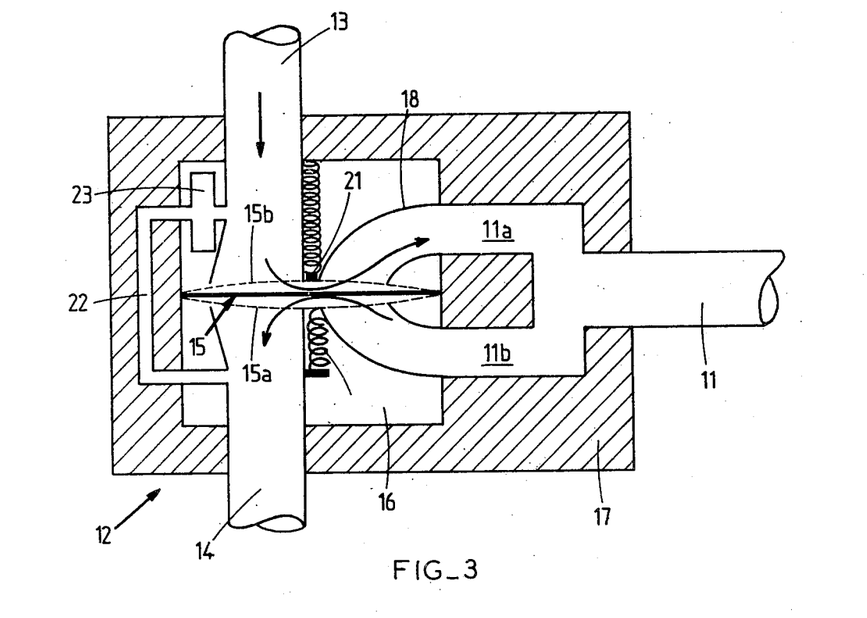
FIG. 3 is an overhead plan view of one embodiment of the electrovalve which is controlled by the electronic device and serves to control the pulsatile unit.

There is shown in FIG. 3 one embodiment of the means for controlling the pulsatile unit 6 in synchronism with the heartbeat rate 2. In this example of construction, said control means consist of an electrovalve 12 integrated in the console 7 and operated in dependence on the electronic device, said device being in turn synchronized with the electrocardiogram (ECG).

The electrovalve 12 communicates via the pipe 11 with the interior of the rigid enclosure 9 in which it is capable of alternately creating a vacuum and delivering compressed gas. The electrovalve 12 is supplied via a duct 13 with compressed gas delivered by a generator (not shown in the drawings) and is connected to a vacuum pump (not shown) by means of a duct 14.

The ducts 13, 14 and the pipe 11 terminate in a common chamber 16 provided within the interior of the electrovalve body 17. Said electrovalve is provided with a deformable diaphragm 15 housed within the chamber 16 and attached to the intersection of the pipe 11 and of the ducts 13, 14. The pipe 11 is subdivided into two passages 11a, 11b which are gathered together within the chamber 16 by means of an inwardly curved section 18 traversed in its central zone by the diaphragm 15 which is provided with a possibility of displacement and is thus capable of taking up two distinct positions.

In a first position 15a, the diaphragm 15 is applied against one edge of the connecting passage between the ducts 13, 14 and the inwardly curved section 18, thereby closing the communication between the vacuum duct 14 and the pipe 11. In this position 15a, the diaphragm 15 therefore permits the flow of compressed air from the duct 13 to the section 18 and the pipe 11.

In the second position 15b, the flexible diaphragm 15 is applied in leak-tight manner against the opposite edge of the communication opening between the ducts 13, 14 and the section 18 and therefore shuts-off the admission of compressed gas into the pipe 11 while at the same time establishing a communication between the vacuum duct 14 and the pipe 11.

The electrovalve 12 is equipped with a spring 19, one end of which is attached to the central portion of the diaphragm 15 which is continuously urged by the spring to its position 15b. In addition, the sliding armature of an electromagnet 21 is attached to the central zone of the diaphragm 15 in order to bring this latter into its position 15b when the electromagnet is energized.

In accordance with a distinctive feature of the invention, the compressed gas admission duct 13 is shunted on the vacuum duct 14 via a duct 22 and via a buffer reservoir 23 of small cross-sectional area in comparison with the cross-sectional areas of the ducts 13 and 14. In consequence, when the diaphragm 15 is applied in its position 15a as a result of the vacuum created within the duct 14, there remains a low compressed gas pressure on that face of the diaphragm which is directed towards the vacuum duct 14 since gas continues to be supplied on that side by the reservoir 23 and the shunt duct 22.

This arrangement limits the pressure difference between the two faces of the diaphragm 15 and facilitates displacement of said diaphragm from the first position 15a to its second position 15b when the electromagnet 15a is energized.

The operation of the electrovalve 12 for controlling the pulsatile unit 6 during a cardiac cycle is as follows.

During a systole, the energized electromagnet 21 brings and maintains the diaphragm 15 in its position 15a, thus shutting-off the admission of compressed gas into the pipe 11 which therefore communicates with the vacuum duct 14. Since a vacuum is established within the enclosure 9, the envelope 8 is inflated and filled with arterial blood (situation A in FIG. 5) whilst the balloon 5a is deflated and allows the vitiated blood to leave the heart 2 and flow towards the lungs (as shown in FIG. 6A). At the beginning of the following diastole, the electromagnet 21 is de-energized, the spring 19 returns the diaphragm 15 to its position 15b, thus interrupting the communication between the vacuum duct 14 and the pipe 11 which is then supplied with compressed air.

In consequence, the pressure within the interior of the enclosure 9 compressed the envelope 8 and discharges the arterial blood contained within this latter to the catheter 5 which inflates and obstructs the coronary sinus 1 (situation B in FIG. 5 and FIG. 6B). The arterial blood is then injected through the vena cava 20 or major vein of the heart into the zone to be irrigated.

The changeover from position 15a to position 15b of the diaphragm 15 is facilitated by the shunt constituted by the duct 22 and the buffer reservoir 23.

The electrovalve 12 thus operates by alternately admitting compressed gas into the pipe 11 and by creating a vacuum within this latter at each cardiac cycle.

Figure 4:
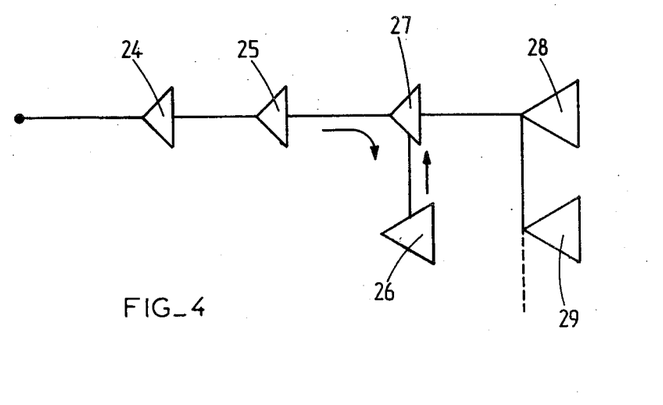
FIG. 4 is a block diagram of the electronic follow-up control device.

The description which now follows relates to the electronic device for controlling the electrovalve 12 and the pulsatile unit 6 in dependence on the electrocardiogram of the patient, reference being made more particularly to FIGS. 2, 4 and 8.

This device comprises the following essential constituent elements:

(1) an amplifier 24 (shown in FIG. 4) for continuously displaying the analog curve of the electrocardiogram (ECG) of the patient on the screen of the console 7;

(2) an analog-to-digital converter 25 connected to the amplifier 24 for displaying on the screen digital signals (curve A) which correspond to the curve of the electrocardiogram (ECG). It is thus apparent from FIG. 8 that the converter 25 displays on the screen digital signals (A1-A2) corresponding to the systole peaks (R) of the electrocardiogram;

(3) a delay device 26 connected to the converter 25 and capable of delaying the digital signals A1, A2 by a predetermined time interval whilst the signals thus delayed are displayed on the screen are represented by a curve B;

(4) a trigger circuit 27 connected to the delay device 26 and capable of generating a command signal C for initiating operation of the electrovalve 12, said trigger circuit being turned-on by a digital signal from the delay device 26 during a systole (S);

(5) elements for displaying on the screen the real curve B of the consecutive pressure variation within the electrovalve 12, and the signals D' representing the real curve of the retroperfusion blood flow.

In the diagram of FIG. 8, it is apparent that the digital signals of curve B are displaced by a time interval $\theta_1$ with respect to the digital signals (A1, A2), that the command signal C extends over a time interval T1 which begins during a systole (S) and ends during the following diastole (D). Finally, the real curve D attains its maximum after a time interval $\theta_2$ which follows the initial instant of the command signal C.

The trigger circuit 27 is connected to power amplifiers 28, 29 . . .

In accordance with a distinctive feature of the invention, the apparatus is also provided with a fluxmeter 31 which is connected between the pulsatile unit 6 and the catheter 5, and connected to the console 7 by means of a pipe 32 (as shown in FIGS. 1 and 2).

The intended function of the fluxmeter 31 is to compare the real blood flow from the pulsatile unit 6 with the flow controlled from the electropneumatic console 7 in order to permit a modulation of the real blood flow so that this latter may be continuously adapted to the cardiac cycle of the patient in accordance with the electrocardiogram (ECG). In other words, the fluxmeter 31 controls the real blood flow in dependence on the electrocardiogram (ECG) while transmitting its blood-flow measurements to the electronic device.

The invention also proposes to connect a syringe 33 on the tube 3 downstream of the pulsatile unit 6 and of the fluxmeter 31. The design function of the syringe 33 is to permit injection of cardiotropic medications into the heart 2 at infinitesimal doses. The syringe 33 can be actuated by any suitable means, for example electrically or else either pulsed or suitably programmed. The cardiotropic medications are intended in particular to reduce the effects of an infarction or of coronary ischemia.

The invention further provides for the patient's safety by equipping the apparatus with a cardiac arrythmia detector (of a type known per se and not shown in the drawings). This detector is adapted to cooperate with the electronic device and the electrovalve 12 in order to transmit to this latter an order for immediate deflation of the balloon 5a of the catheter 5 in the event of appearance of an extrasystole R1 (FIG. 8) on the electrocardiogram (ECG).

In this case, the converter 25 digitizes the extrasystole R1 by generating a corresponding signal A'2, the trigger circuit 27 delivers the order to the electrovalve 12 to immediately cut-off the admission of compressed gas into the pulsatile unit 6, these signals being shown in dashed lines in FIG. 8. In consequence, the balloon 5a is deflated as soon as the extrasystole R1 appears, thus providing a passageway for the flow of vitiated blood from the coronary sinus (as shown in FIG. 6A).

Thus any risk of accident during retroperfusion is removed.

Figure 7A:
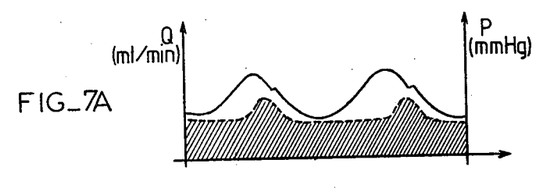
FIG. 7A is a diagram showing the arterial pressure and the venous pressure during a single cardiac cycle.
Figure 7B:
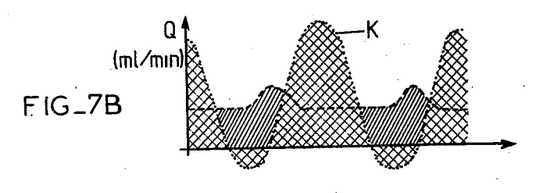
FIG. 7B is a diagram showing the curve of variation in flow rate of blood injected into the catheter during a single cardiac cycle.

The continuous line of FIG. 7A shows the variation in arterial pressure and the broken line shows the variation in venous pressure during one cardiac cycle of the patient whilst FIG. 7B shows the variation in blood flow Q passed into the catheter 5 (curve K) in synchronism with the cardiac cycle. It is thus apparent that the retroperfused arterial blood flow undergoes an abrupt increase during each diastole and becomes negative during the systoles.

FIG. 6A shows the balloon 5a in the deflated state during a systole in order to permit departure of the vitiated blood to the lungs whereas FIG. 6B shows the balloon 5a in the deflated state during a diastole and injection of arterial blood into the coronary sinus 1.

Figure 9:
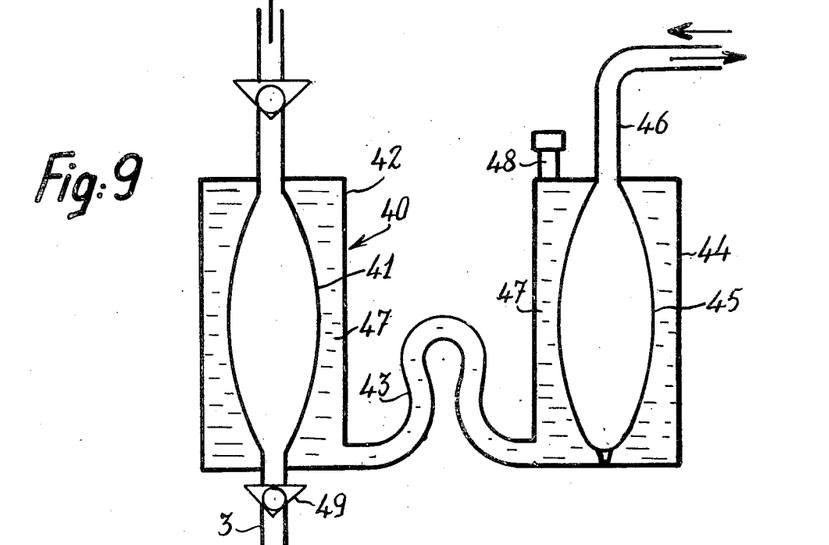
FIG. 9 is a view in elevation showing a second embodiment of the pulsatile unit which is controlled by the electrovalve of FIG. 3.

There is shown in FIG. 9 a second embodiment of the apparatus contemplated by the invention, in which the pulsatile unit 40 comprises an inflatable flexible envelope 41 which forms an integral part of the tube 3 and, as in the previous embodiment, communicates with the arterial system 4 at one end and with the venous system 20 at the other end. The pulsatile unit 40 further comprises a rigid enclosure 42 which contains the envelope 41 in leak-tight manner. Said enclosure 42 communicates via a pipe 43 with a second enclosure 44 which contains a flexible envelope 45. Said envelope 45 is attached to the wall of the enclosure 44 and opens into a duct 46 through which it is possible either to inject compressed gas or to create a vacuum within said envelope. The space formed between the two envelopes 41, 45 and the walls of the enclosures 42, 44 is filled with a liquid 47 such as water. To this end, the enclosure 44 is provided with a filler inlet nozzle 48. In addition, a non-return valve 49 is mounted on the tube 3 immediately upstream of the pulsatile unit 40.

The operation of this device is as follows: when compressed air is blown into the flexible envelope 45, this latter becomes inflated and the liquid 47 compresses the flexible envelope 41, thus driving the arterial blood contained within the envelope 41 towards the coronary sinus. Conversely, when a vacuum is created within the envelope 45, the liquid 47 flows back from the enclosure 42 into the enclosure 44; the envelope 41 becomes inflated and is filled with arterial blood which is driven towards the patient's heart when compressed gas is again blown into the envelope 45.

Figure 10:
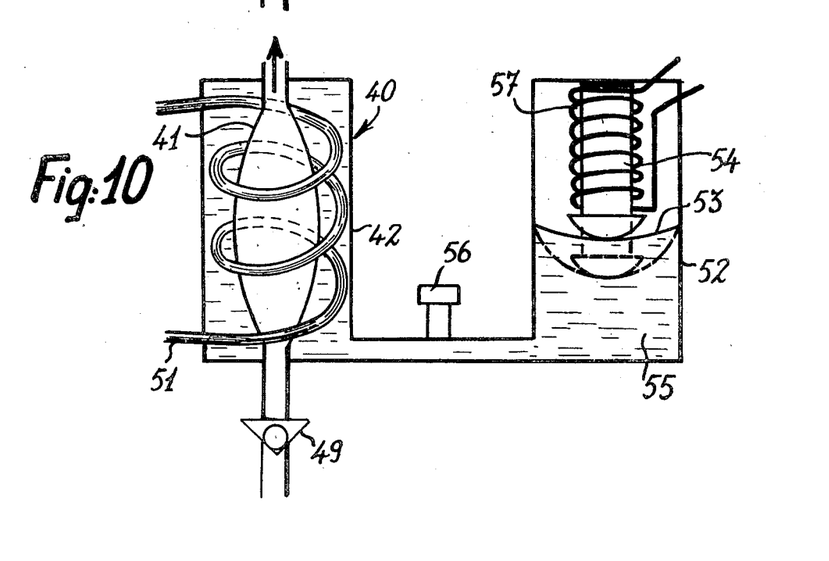
FIG. 10 is a view in elevation showing a third embodiment of the apparatus in which the pulsatile unit is controlled by an electromagnetic device instead of the pneumatic electrovalve.

In the alternative embodiment shown in FIG. 10, the pulsatile unit 40 is similar to the pulsatile unit of FIG. 9, with the exception of a tube coil 51 which penetrates into the enclosure 42, surrounds the envelope 41 and then passes out of the enclosure 42.

Said tube coil 51 contains a liquid at a preset temperature and is intended to cool the blood contained within the envelope 41 to a predetermined extent, for example in order to reduce its temperature to 34° C. or 32° C. On the other hand, the enclosure 42 communicates with a container 52 closed by an elastic diaphragm 53 which is fixed within the interior of the container 52. The magnetized plunger core 54 of an electromagnet (not shown in the drawings) produces action on said diaphragm and is controlled by the electronic device (7, 24–29) or more precisely by the amplifiers (28, 29).

The space delimited between the enclosure 42, the envelope 41 and the diaphragm 53 is filled with a liquid 55 such as water, a filler inlet nozzle 56 being provided for this purpose. The reciprocating movements of the plunger core 54 are controlled by a winding 57 arranged coaxially with the plunger core 54 and connected to the amplifiers 28, 29.

When the electric current flows in one direction within the winding 57, the plunger core 54 is repelled and thrusts the diaphragm 53 downwards to the position shown in a chain-dotted line. The liquid 55 therefore compresses the envelope 41. Conversely, when the current is reversed, the plunger core 54 undergoes an upward displacement and the liquid 55 flows back into the container 52 whilst the flexible envelope 41 becomes inflated as it is filled with arterial blood.

In this alternative embodiment as in the embodiment shown in FIG. 9, the tube 3 is equipped with a non-return valve 49 whose function is to prevent the arterial blood contained within the pulsatile unit 40 to flow back in the upstream direction. As can readily be apparent, a non-return valve of this type can also be placed in the pipe of FIGS. 1 and 2.

Figure 11:
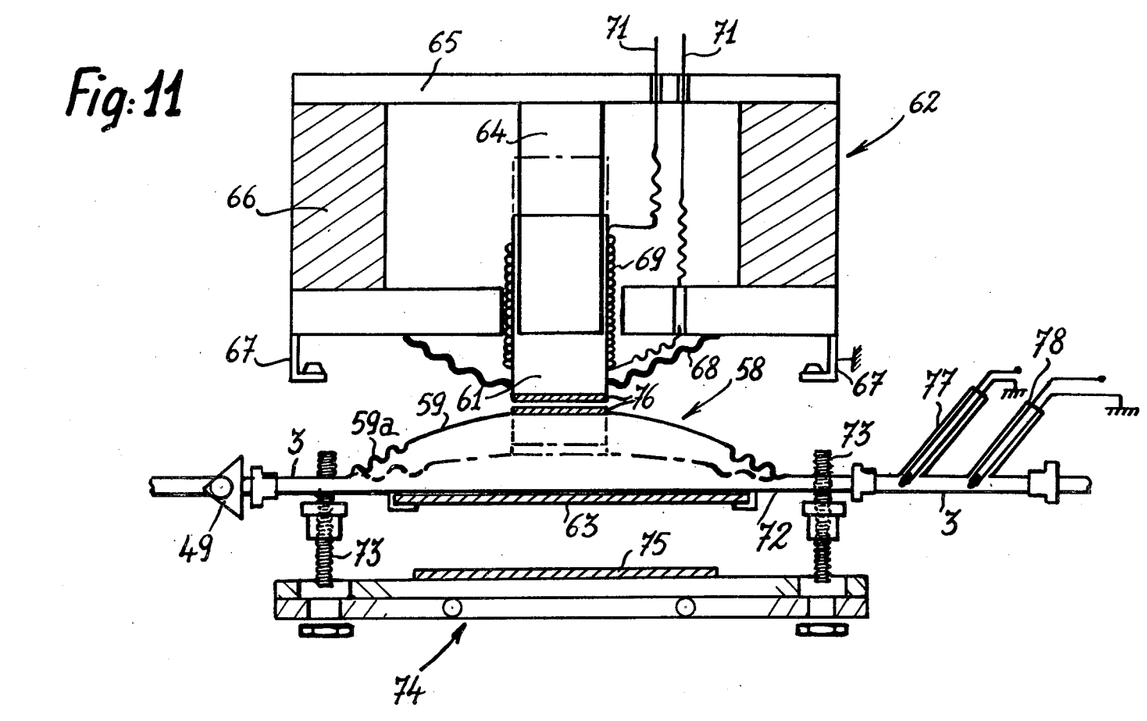
FIG. 11 is a half-sectional half-elevation view of a fourth embodiment of the apparatus, showing another form of construction of the pulsatile unit and of its control device.
Figure 12:
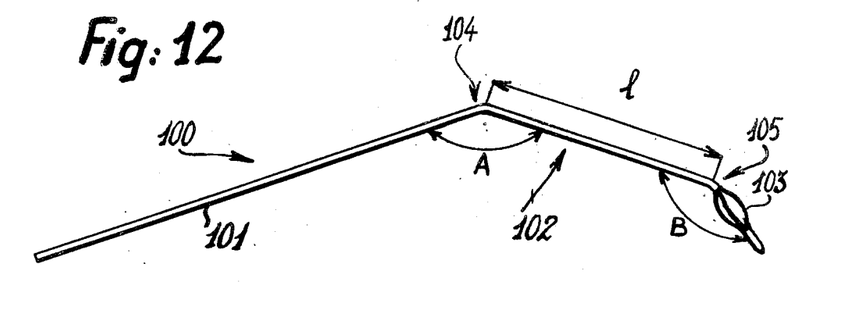
FIG. 12 is a view in elevation showing a preferred embodiment of the balloon catheter which forms part of the equipment according to the invention.
Figure 13:
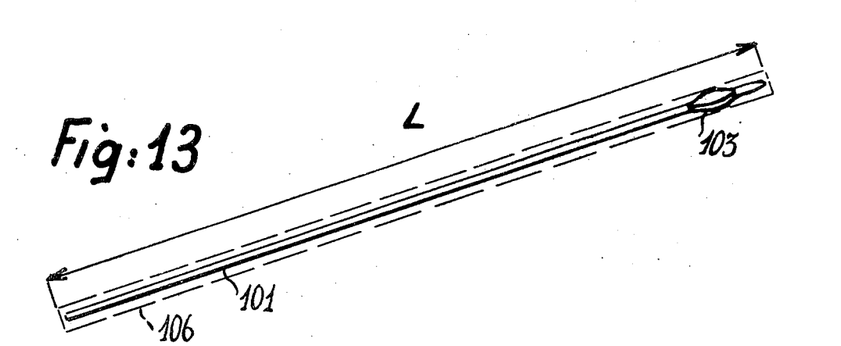
FIG. 13 is a view in elevation showing the catheter of FIG. 12, said catheter being housed within a tubular prestressing guide prior to use.

FIG. 11 illustrates a fourth possible embodiment of the apparatus according to the invention in which the pulsatile unit 58 comprises a flexible envelope 59 which is directly deformable under the action of a moving coil 61 of an electromagnetic control device 62.

One of the faces of the inflatable flexible envelope 59 is applied against a rigid plate 63 in order to have a flat configuration on that side whereas the other face of the envelope is deformable and adapted to cooperate with the coil 61 which is slidably mounted around a guide column 64, said column being attached to the armature 65 of an electromagnet 66 provided with support brackets 67 for mounting this latter on a frame (not shown in the drawings). Since the envelope 59 is applied on the horizontal plate 63, the coil 61 and the electromagnet 66 are placed above the envelope 59 so as to ensure that the lower end of the coil 61 is practically in contact with the envelope 59 when this latter is in the distended and stretched condition.

An elastic annular diaphragm 68 having bellows-type pleats is attached on one side to the lower end of the coil 61 and on the other side to the lower portion of the armature 65 in order to support the coil 61 while permitting a predetermined range of displacement of this latter on the guide column 64. A winding 69 is fixed in a coaxial position with respect to the coil 61 and connected to the amplifiers 28, 29 by means of leads 71 (as shown in FIG. 4).

The plate 63 is secured to a carrier-plate 72 provided with screws 73 for the attachment of a Pelletier cryostatic cell 74 constructed in accordance with a design which is already known per se. Said cell is provided with a thermal conductor 75 for cooling the blood contained within the envelope 59 when this latter is pressed against the plate 63.

The lower end of the coil 61 is fitted with a first magnetized pellet 76, a second pellet 76 which is similar to the first being fixed beneath this latter on the central portion of the envelope 59. The design function of said pellets 76 is to permit inflation of the envelope 59 by mutual attraction when the coil 61 undergoes an upward displacement. Furthermore, the base of the envelope 59 is provided with a corrugated annular reinforcement 59a and probes 77, 78 are mounted on the tube 3 downstream of the pulsatile unit 58 in order to control respectively the blood flow rate and the blood temperature. A probe (not shown) for measuring the viscosity of the blood can also be connected to the tube 3.

The operation of this alternative embodiment is as follows:

when the current corresponding to the digital signals represented in FIG. 8 is in the systole phase, the electromagnetic field produced by the winding 69 attracts the coil 61 which moves upwards in sliding motion on the guide column 64 to the position illustrated in chain-dotted lines and is accompanied by the diaphragm 59 which becomes inflated, this upward displacement of the diaphragm being made possible by the two pellets 76 which are maintained in contact with each other. During the upward displacement of the coil 61, the envelope 59 is therefore inflated with arterial blood. When the current which flows through the winding 69 corresponds to the following diastole, the magnetic field produces a downward displacement of the coil 61 and this latter thus compresses the envelope 59 which reaches the position illustrated in chain-dotted lines, with the result that the blood contained within said envelope is driven into the coronary sinus. The cycle begins again at the following systole.

The Pelletier cell 74 advantageously produces a predetermined cooling action on the blood by reducing the temperature to 32° C. or 34° C., for example.

In regard to the alternative embodiments illustrated in FIGS. 9 and 10, it should be noted that, by providing a flexible envelope 41 surrounded by a liquid 47 or 55, this removes any danger of accidental failure of the envelope 41 arising, for example, from possible faulty operation of the vacuum pump or of the compressed gas generator as a result of an error made by the operator. In fact, if the envelope 41 where to be torn as a result of an accidental operation of this type, there would be a potential danger of delivery of compressed gas into the patient's heart and of gaseous obstruction. On the contrary, if such a faulty operation were to take place when adopting the devices of FIGS. 9 and 10, there would accordingly be a failure of the envelope 45 or the diaphragm 53 but not of the envelope 41. In consequence, diastolic injection of blood would simply be discontinued without any attendant danger of a cardiac accident.

The apparatus according to the invention is therefore capable of carrying out retroperfusion of arterial blood in a heart affected by an infarct with a maximum degree of safety and in perfect synchronization with the electrocardiogram of the patient. This synchronized diastolic retroperfusion of the coronary sinus constitutes an essential application of the apparatus contemplated by the invention. However, this apparatus can also be employed for the treatment of other ischemias of the body such as, for example, ischemia of the brain or of the lower limbs, hepatic ischemia, abdominal ischemia and so forth, with a possibility of injecting suitable medications or drugs in the areas involved.

It is also important to note that blood jets can be retroperfused not only at each diastole of the cardiac cycle but only once out of two or once out of four diastoles or even once out of eight diastoles by suitably programming the electronic control device and using the patient's electrocardiogram as a basis.

Referring now to FIGS. 12 to 18, a preferred embodiment of the catheter which forms part of the apparatus according to the invention will now be described.

In the first place, the catheter 100 comprises a tube 101 of material having an elastic memory and so designed that, when it is not subjected to prestress, its end portion 102 equipped with the flexible balloon 103 has two elbows 104, 105. The first elbow 104 is located at a predetermined distance 1 which is preferably in the vicinity of seven centimeters from the second elbow 105. The elbow 104 is bent at an obtuse angle A approximately within the range of 130 to 150 degrees whilst the second elbow 105 which is located immediately before the balloon 103 is bent at an angle B approximately within the range of 120 to 150 degrees. The total length L of the tube 101 (shown in FIG. 13, can have a maximum value of 40 centimeters in order to avoid any increase in resistance to the flow of blood and therefore to reduce the retroperfused flow as has been demonstrated by tests performed on the corpse. The material chosen for the fabrication of the tube 101 must have an elastic memory and accordingly consists, for example, of polyvinyl chloride. Under these conditions, since the tube 101 is pre-formed so as to provide the two elbows 104 and 105 with included angles A and B within the limits stated earlier, said tube can be maintained rectilinear prior to use by passing it through a tubular guide 106. When the tube is passed out of said guide 106, the catheter as a whole assumes the shape shown in FIG. 12 as a result of resilient recovery and is ready for use in order to inject oxygenated blood into the coronary sinus.

Figures 15, 18:
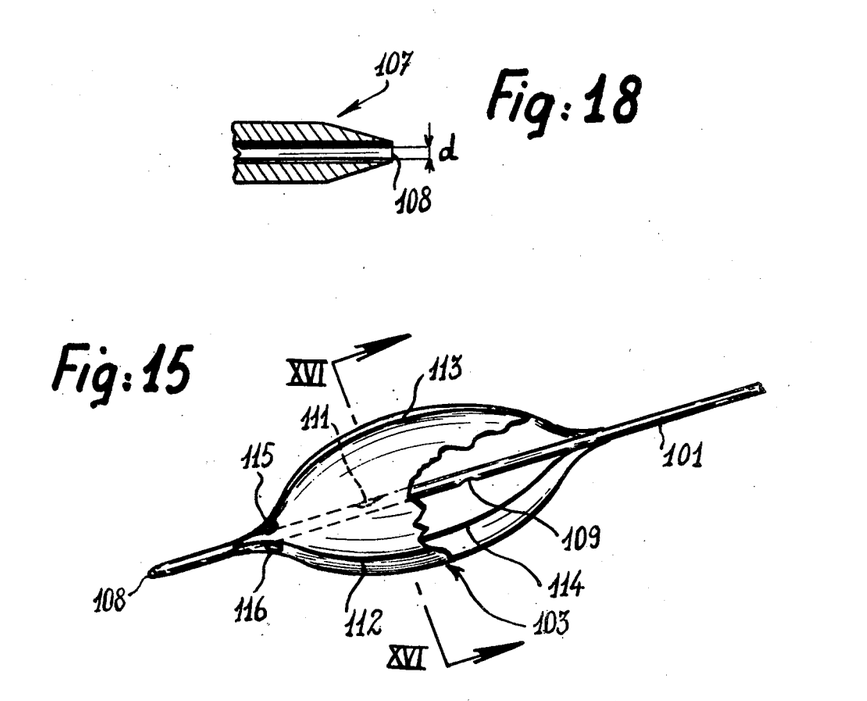
FIG. 15 is a cutaway view in perspective showing the balloon of the catheter and its internal tube.
FIG. 18 is an axial sectional view of the distal end of the catheter of FIGS. 12 to 17.

Said catheter is further distinguished by the following features: in the first place, the tube 101 must have an internal diameter d (as shown in FIG. 18) of at least 1.5 mm in order to permit a fluid flow rate which must be within the range of 50 to 100 milliliters per minute. In fact, tests have shown that it is the internal diameter d of the catheter orifice which is important and not the external diameter. Studies which have led to this result have been made in vitro and on an animal preparation. They have shown that, in the case of pulsatile operation in which the oscillation frequency is lower than 10 Hz (as is the case in human beings and in animals), the capacitance of the circuit and the inertance affect the flow through the catheter only by 5%. Under these conditions, the resistance to the flow conforms to the Poiseuille laws.

Moreover, the distal end 107 of the catheter 100, namely the end located downstream of the balloon 103 must be tapered as shown in FIG. 18 in order to permit percutaneous insertions. However, the tapered shape of the end portion 107 must not produce a reduction in the internal diameter d of the distal orifice 108, as shown in FIG. 18. The flexible balloon 103 is placed at a distance e (shown in FIG. 14) of at least eight millimeters from the distal orifice 108. In the portion located within the interior of the balloon 103, the tube 101 is pierced by a maximum number of two holes 109, 111 which are located in relatively displaced relation and provide a communication between the orifice of the tube 101 and the interior of the balloon 103. The minimum distance e=8 mm between the distal orifice 108 and the balloon 103 results from anatomical studies and a number of different experiments performed. In regard to the holes 109, 111, the limitation to a maximum number of two holes and the relative displacement of these latter prevent any impairment of rigidity of the catheter which would otherwise result from a larger number of communication holes between the tube and the interior of the balloon. Tests have in fact demonstrated that, when more than two holes are formed in the tube, there is a potential danger of tube failure at the time of insertion or withdrawal operations. Correlatively, the fact that the holes are not drilled opposite to each other but in relatively displaced locations in the longitudinal direction constitutes a safety measure which is added to the limitation to two holes.

According to another distinctive feature of the invention, the balloon is fabricated from material selected so as to ensure that inflation and deflation of said material take place entirely along the horizontal portion of a sigmoid stress-strain curve (known per se and not shown in the drawings), thereby making it unnecessary to utilize the elasticity of the material which can accordingly consist of polyurethane or polyvinyl chloride.

Figure 14:
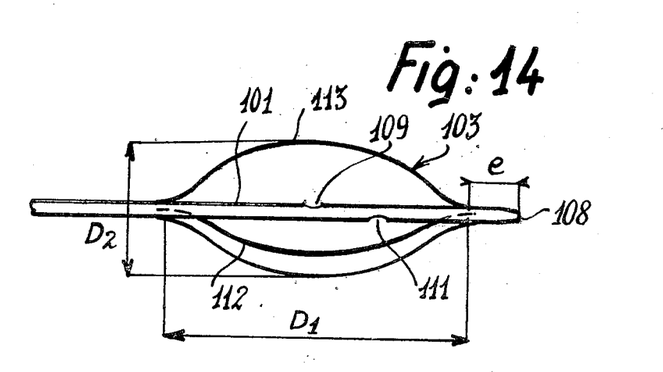
FIG. 14 is a view in elevation to a larger scale showing the balloon of the catheter and the tube which passes through said balloon.

The balloon 103 must have an ovoid shape which is shown in FIGS. 14 and 15 and especially permits adaptation of said balloon to the lumen of the coronary sinus as demonstrated by studies on a corpse. Under these conditions, the balloon 103 in the inflated state has an ovoid shape such that the longest diameter $D_1$ is coaxial with the tube 101, the transverse diameter $D_2$ being consequently smaller than $D_1$.

According to another important feature, the balloon 103 is provided with reinforcement strips 112, 113, 114 which extend from one end to the other. These strips 112–114 are rigid and angularly displaced with respect to each other. In the exemplified embodiment illustrated in the drawings, provision is made for three strips 112–114 separated by equal angular sectors of 120 degrees. Said strips can be formed, for example, by deposition of polyvinyl chloride on the flexible material of the balloon 103 in a manner known per se.

Figure 16:
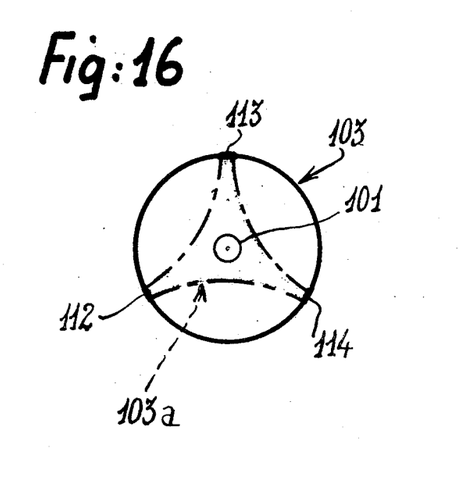
FIGS. 16 and 17 are transverse sectional views of the balloon respectively in the inflated state and in the deflated state.
Figure 17:
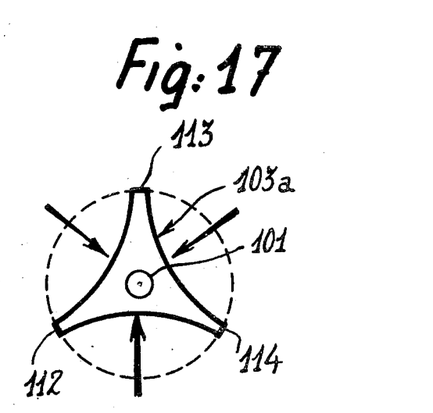

Under these conditions the balloon has the configuration illustrated in FIG. 16 when it is in the inflated state. When the balloon is deflated, its sectors located between the rigid strips 112–114 collapse so as to take up the position 103a shown in chain-dotted lines in FIG. 16 and in full lines in FIG. 17 whilst the rigidity of the strips 112–114 has the effect of maintaining these latter in position. The balloon as a whole then has the appearance shown in FIG. 17, in which it affords minimum resistance to the flow of blood during a systole.

Finally, experiments performed on animals have shown that it is necessary to maintain a slight leakage at the level of the ring which serves to fasten the balloon 103 on the tube 101, on the side corresponding to the distal end of said tube. To this end, the downstream end of the balloon 103 is pierced by at least one orifice 115 (two orifices 115, 116 are shown in the example of FIG. 15). Said orifice or orifices are so dimensioned as to permit a small leakage flow of the fluid during inflation of the balloon 103. This small leakage flow at the level of the fastening ring has two advantages: in the first place, it prevents the formation of blood clots within the interior of the balloon 103 when this latter is filled with blood and, in the second place, it removes any danger of failure of the balloon in the event of excess pressure.

Finally, experiments on animals have shown that, in order to be really effective without producing a traumatic effect, the volume of the balloon 103 must be approximately within the range of 0.5 to 1.5 milliliters.

The invention is not limited to the embodiments hereinabove described and may accordingly extend to a large number of alternative modes of execution.

By way of example, oxygenated venous blood can be supplied to the apparatus according to the invention instead of arterial blood and can be withdrawn by means of a suction pump system (such as a disk-type pump, for example) in order to supply the pulsatile unit at a flow rate which can be imposed, thus making it possible to dispense with the flowmeter. The apparatus according to the invention can thus be employed for collecting oxygenated blood from the renal veins. In the alternative embodiment of FIG. 11, provision can also be made for a second flexible diaphragm beneath the diaphragm 50, a liquid being intended to fill the intercalary space between these two diaphragms. This arrangement provides additional safety as well as better distribution of the pressure of the plunger core 61 on the blood.

What is claimed is:

1. A blood retroperfusion apparatus comprising:
   a connecting tube open at both ends and adapted to connect a source of oxygenated blood and the zone to be irrigated;
   a flexible-balloon catheter provided on the end of said tube which is adapted to be engaged in the zone to be irrigated, said balloon comprising reinforcement means extending in the longitudinal direction;
   a pulsatile unit arranged on said tube and connected to control means whereby a predetermined quantity of oxygenated blood can be driven periodically by said unit towards the catheter;
   an electronic device for maintaining the pulsatile unit and its control means in step with the patient's heartbeat rate;
   and means to synchronize said device with an electrocardiogram (ECG) of the patient in order to control the injection of blood into the coronary sinus by means of the pulsatile unit and to allow the vitiated blood to flow back in the opposite direction during a systole.

2. An apparatus according to claim 1, wherein the reinforcement means provided on the balloon comprises strips which extend from one end of the balloon to the other, said strips being rigid and angularly spaced apart in order to remain in their initial positions at the time of each deflation of the balloon between said strips.

3. An apparatus according to claim 2, wherein said strips are three in number and are equally spaced apart.

4. An apparatus according to claim 1, wherein the pulsatile unit comprises an inflatable flexible envelope forming an integral part of the tube and adapted to communicate at one end with the high-pressure arterial system and at the other end with the low-pressure venous system, and a rigid enclosure within which the flexible envelope is housed in leak-tight manner, said enclosure being connected to said control means via a pipe which can be alternately filled with compressed gas and evacuated under the action of said control means in order to exert a correlative compressive force on the flexible envelope which is filled with arterial blood while driving the blood towards the catheter and then to interrupt the flow of blood towards the catheter by initiating a further inflation of the envelope with arterial blood.

5. An apparatus according to claim 4, wherein the means for controlling the pulsatile unit comprise an electrovalve operated in dependence on the electronic device which is in turn synchronized with the electrocardiogram (ECG) and said electrovalve communicates via the pipe with the interior of the enclosure in which said electrovalve alternately creates a vacuum and delivers compressed gas by means of corresponding connections with a compressed-gas generator and with a vacuum pump.

6. An apparatus according to claim 5, wherein the electrovalve comprises a deformable diaphragm fixed at the intersection of the pipe, of the compressed-gas duct and of the vacuum duct in order to occupy under the action of an electromagnet a first position in which said diaphragm permits the introduction and transfer of compressed gas through the pipe to the pulsatile unit and, under the action of an elastic restoring member, a second position in which said diaphragm puts the pipe into communication with the vacuum duct and interrupts the admission of compressed gas.

7. An apparatus according to claim 6, wherein the compressed-gas duct is shunted on the vacuum duct by means of a duct and a buffer reservoir having a small cross-sectional area in comparison with the cross-sectional area of the vacuum duct and of the compressed-gas duct in order to limit the pressure difference between the two faces of the diaphragm and to facilitate unseating followed by displacement of said diaphragm from the first position to the second position.

8. An apparatus according to claim 5, wherein the electronic device comprises:
   an amplifier for continuously displaying the analog curve of the patient's electrocardiogram (ECG) on the screen of a console;
   an analog-to-digital converter connected to the amplifier for displaying digital signals corresponding to the curve of the electrocardiogram (ECG) on the screen of the console;
   a delay device connected to the converter and capable of delaying the digital signals corresponding to the systoles while the signals thus delayed are displayed on the screen and represented by a curve;
   a trigger circuit connected to the delay device and capable of generating a command signal for initiating the operation of an electrovalve, said trigger circuit being turned-on by a signal from the delay device during a systole;
   elements for displaying on the screen the real curve of the consecutive pressure variation within the electrovalve and the real curve of the retroperfusion blood flow.

9. An apparatus according to claim 1, wherein said apparatus comprises a fluxmeter connected between the pulsatile unit and the catheter, said fluxmeter being adapted to compare the real blood flow with the controlled flow in order to permit modulation of said real flow, as well as a syringe connected on the tube downstream of the pulsatile unit for injection of cardiotropic medications into said tube.

10. An apparatus according to claim 1, wherein the pulsatile unit comprises an inflatable flexible envelope forming an integral part of the tube and adapted to communicate with the high-pressure arterial system at one end and with the low-pressure venous system at the other end, and a first rigid enclosure containing said envelope in leak-tight manner, said first enclosure being adapted to communicate with a second enclosure containing a flexible envelope which can be alternately filled with compressed gas and evacuated by the control means aforesaid, the internal spaces formed between the two flexible envelopes and the two enclosures being filled with liquid and communicating with each other.

11. An apparatus according to claim 1, wherein the pulsatile unit comprises an inflatable flexible envelope forming an integral part of the tube and adapted to communicate with the arterial system at one end and with the venous system at the other end, and a rigid enclosure containing said flexible envelope in leak-tight manner, said enclosure being adapted to communicate with a container closed by an elastic diaphragm on which the plunger core of an electromagnet produces action under the control of the electronic device in order to initiate successive inflation and deflation of said flexible envelope in correlation with the electrocardiogram (ECG) of the patient, said enclosure and said container being filled with a suitable liquid for transmitting the movements of said diaphragm to said envelope.

12. An apparatus according to claim 1, wherein the pulsatile unit comprises an inflatable flexible envelope forming part of the tube, one face of said envelope being applied against a rigid plate whilst the other deformable face is adapted to cooperate with the moving coil of an electromagnetic device, the displacements of said moving coil being controlled by a winding connected to the electronic control device so that said moving coil either compresses or inflates the envelope as a function of the direction of the electric current which flows through said winding.

13. An apparatus according to claim 1 and a suction pump for supplying the pulsatile unit with oxygenated venous blood.

14. An apparatus according to claim 1, wherein the catheter comprises a tube of material having an elastic memory and so designed as to ensure that the tube end portion equipped with the catheter balloon has two elbows when the tube is not subjected to prestress, the first elbow located at a predetermined distance from the second elbow being inclined at an obtuse angle approximately within the range of 130 to 150 degrees whilst the second elbow located immediately upstream of said balloon is inclined at an angle approximately within the range of 120 to 150 degrees.

15. An apparatus according to claim 14, wherein the catheter tube has an internal diameter of at least 1.5 mm so as to permit a flow rate of fluid within the range of 50 to 100 milliliters per minute whilst the maximum length of said tube is approximately 40 cm, the distance between the two elbows being approximately 7 cm.

16. An apparatus according to claim 14, wherein the distal end of the catheter tube located downstream of the balloon is tapered for percutaneous insertions but without any reduction in the internal diameter of said tube.

17. An apparatus according to claim 14, wherein the flexible balloon is placed at least at a distance of 8 mm from the distal orifice of the tube and said tube is pierced within the interior of said balloon with a maximum number of two holes which provide a communication between the orifice of said tube and the interior of said balloon.

18. An apparatus according to claim 14, wherein the balloon is fabricated from material chosen so as to ensure that inflation and deflation of said balloon takes place entirely on the horizontal portion of a sygmoid stress-strain curve in order to avoid the need to utilize the elasticity of the material and the balloon in the inflated state has an ovoid shape such that the longest diameter is coaxial with the tube.

19. An apparatus according to claim 18, wherein the material of the balloon is selected from the group consisting of polyurethane and polyvinyl chloride.

20. An apparatus according to claim 1, wherein at least one hole is formed at that end of the catheter which is located nearest the distal orifice of the tube, said hole being so dimensioned as to permit a small leakage flow of fluid during inflation of the catheter which has a volume approximately within the range of 0.5 to 1.5 milliliter in the inflated state.

* * * * *